(12) United States Patent
Ruppersberg

(10) Patent No.: US 11,471,114 B2
(45) Date of Patent: Oct. 18, 2022

(54) MEDICAL SYSTEM FOR MAPPING OF ACTION POTENTIAL DATA

(71) Applicant: Ablacon Inc., Wheat Ridge, CO (US)

(72) Inventor: Peter Ruppersberg, Blonay (CH)

(73) Assignee: Ablacon Inc., Wheat Ridge, CO (US)

( * ) Notice: Subject to any disclaimer, the term of this patent is extended or adjusted under 35 U.S.C. 154(b) by 215 days.

(21) Appl. No.: 16/071,387

(22) PCT Filed: Jan. 19, 2016

(86) PCT No.: PCT/EP2016/000087
§ 371 (c)(1),
(2) Date: Jul. 19, 2018

(87) PCT Pub. No.: WO2017/125114
PCT Pub. Date: Jul. 27, 2017

(65) Prior Publication Data
US 2021/0174931 A1 Jun. 10, 2021

(51) Int. Cl.
*A61B 5/00* (2006.01)
*G16H 20/40* (2018.01)
(Continued)

(52) U.S. Cl.
CPC ............ *A61B 5/743* (2013.01); *A61B 5/287* (2021.01); *A61B 5/339* (2021.01); *A61B 5/6852* (2013.01);
(Continued)

(58) Field of Classification Search
None
See application file for complete search history.

(56) References Cited

U.S. PATENT DOCUMENTS

| 10,888,236 B2 * | 1/2021 | Ruppersberg | A61B 5/6858 |
| 2007/0073179 A1 * | 3/2007 | Afonso | A61B 5/287 |
| | | | 600/523 |

(Continued)

*Primary Examiner* — Nancy Bitar
(74) *Attorney, Agent, or Firm* — Woods Patent Law, P.C.

(57) ABSTRACT

The present invention concerns a Medical system for mapping of action potential data comprising an elongated medical mapping device (1) suitable for intravascular insertion having an electrode assembly (80) located at a distal portion (3) of the mapping device (1), a data processing and control unit (15) for processing data received from the mapping device (1), the data processing and control unit including a model generator for visualizing a 3-dimensional heart model based on one of electrical navigation system, MRI or CT scan data of a heart, a data output unit (16) for displaying both the 3-dimensional heart model and the processed data of the mapping device (1) simultaneously in a single visualization, wherein the model generator is configured to structure 3D scan data of the heart into 6 directions (a, b, c, d, e or f) of a cube, each direction is associated with a separate Cartesian coordinate system with $X^{(a, b, c, d, e \, or \, f)}$, $Y^{(a, b, c, d, e \, or \, f)}$, $Z^{(a, b, c, d, e \, or \, f)}$ coordinates, wherein for assigning each 3D scan data point to one of the 6 directions (a, b, c, d, e or f) the following 6 true or false tests are applied: Formula (I), wherein max indicates the maximum leg length of the respective X, Y or Z axis and wherein mes indicates the measured value of a scanned data point, and wherein the data point is assigned to the direction (a, b, c, d, e or f) for which the test outcome is true.

14 Claims, 8 Drawing Sheets

(51) Int. Cl.
*G16H 50/50* (2018.01)
*G06T 7/00* (2017.01)
*A61B 5/339* (2021.01)
*A61B 5/287* (2021.01)

(52) U.S. Cl.
CPC ........... *G06T 7/0012* (2013.01); *G16H 20/40* (2018.01); *G16H 50/50* (2018.01); *A61B 2576/023* (2013.01); *G06T 2207/10072* (2013.01); *G06T 2207/30048* (2013.01); *G06T 2207/30101* (2013.01)

(56) References Cited

U.S. PATENT DOCUMENTS

| | | | | |
|---|---|---|---|---|
| 2008/0009758 | A1* | 1/2008 | Voth | A61B 5/318 600/523 |
| 2013/0006131 | A1* | 1/2013 | Narayan | A61N 1/0565 606/32 |
| 2014/0088395 | A1* | 3/2014 | Dubois | A61B 5/339 600/382 |
| 2018/0342072 | A1* | 11/2018 | Raudins | A61B 8/4245 |

* cited by examiner

MEDICAL SYSTEM FOR MAPPING OF ACTION POTENTIAL DATA

RELATED APPLICATION

This application is a national stage entry of, and claims priority and other benefits from: (a) International Patent Application PCT/EP2016/000087 to Ruppersberg filed on Jan. 16, 2016, entitled "Medical System for Mapping of Action Potential Data" (hereafter "the '000087 patent application"). The entirety of the '000087 patent application is hereby incorporated by reference herein.

FIELD OF THE INVENTION

The present invention relates generally to a medical system for mapping of action potential data according to claim 1 and to a method for mapping of action potential data according to claim 8.

The present invention especially relates to a medical system for mapping of action potential data with individual features of claim 1 and further to a method for mapping of action potential data with individual features of claim 1.

BACKGROUND

Such medical systems, comprising elongated medical devices suitable for intravascular insertion, such as catheters, especially mapping catheters, and guide wires for guiding catheters through vessels, organs or other body cavities are e.g. used in the treatment of atrial fibrillation (Afib). Atrial fibrillation is the most frequent arrhythmic disorder of the heart. Blood clotting occurring in the fibrillating atria is one main cause of stroke. In so far, Afib is one of the most important disorders associated with a high fatal risk. The cause for Afib has been subject to intensive scientific investigations and is meanwhile largely understood. In most patients, the four pulmonary veins draining into the left atrium are the sources of rapid arrhythmic action potentials which trigger circular excitation patterns ("rotors"), in the left atrium that induce a high frequency fibrillation through their re-entry mechanism. Those rotors have the character of small action potential cyclones of 2 to 3 cm$^2$ in size. The likelihood of occurrence of those rotors and the frequency of pathological action potential generation in the pulmonary veins increases with fibrotic structural changes and certain modifications of ion channel expression patterns in atrial cells with age.

The only potentially curative treatments for Afib are open heart surgery or catheter ablation of those parts of the atrial wall tissue which originate, transmit or maintain the pathologic excitation circles.

Today the use of catheter ablation like open heart surgery is still limited by the potentially fatal risk of some severe side effects associated with the procedure: When the integrity of the atrial wall is destroyed by too intense ablation, perforations of the atrial wall into the pericardium or fistulas into the esophagus can have severe to deadly outcomes. The alteration of the endocardial cells on a larger surface can initiate clotting in the treated atrium which may lead to deadly strokes. That is why the procedure requires full anticoagulation. Last but not least, if the intensity of the ablation is kept too low to avoid those side effects in many cases the therapeutic effect is insufficient and patients face a success rate of the treatment of only 50-70% on average.

To improve the situation, medical systems for mapping of action potential data comprising mapping catheters are used to first identify circular excitation patterns (rotors) in the left atrium and to identify the location of the rotor. After identification of rotors, force sensing catheters are used that allow to better control the catheter positioning force which has an influence on the intensity of ablation. Further, water irrigation tries to keep the endothelial tissue free of lesions and micro-calorimetric sensors try to measure and control the heat in the tissue.

Such medical systems for mapping of action potential data further comprise 3D model generators that form 3D models based on anatomic data to support identification of the location e.g. of a rotor. The models are built from individual triangles of various sizes and are visualized on a display. If a model is colored or carries a surface structure a surface texture is mapped onto these triangles resulting in complex geometric relationships. It is therefore not possible to define the topology of anatomical models such as human atria by simple coordinates in a general topographic system. This makes it very difficult to exactly define the location of surface structures of interest in a cardiological mapping session with a diagnostic catheter and to find the location again for example with a different catheter. Moreover, it is extremely difficult to have a spatial orientation during an electrophysiological session without orienting at very prominent anatomic structures.

EP2641557 A1 discloses a medical system comprising a display console and a control computer connected to the display console. The control computer is configured to produce a map of the determined locations corresponding to the openings of a number of pulmonary veins and a mitral valve. Even though a map of certain anatomical features is generated, orientation information provided by this system is restricted.

US2015254419 A1 discloses a method for displaying summarized physiological mapping data. The method may include storing a set of three-dimensional positional data on a memory, storing a set of metric data on the memory, and storing a set of electrogram data on the memory. The method may also include outputting the set of three-dimensional positional data, the set of two-dimensional metric data, and the set of electrogram data from the memory to a display unit and displaying the set of three-dimensional positional data, the set of two-dimensional metric data, and the set of electrogram data on the display unit as a summarized static display. Even though three-dimensional positional data are available, it is extremely difficult to have a spatial orientation during an electrophysiological session without orienting at very prominent anatomic structures.

SUMMARY

It is hence an object of the present invention to provide an improved medical system for mapping of action potential data which provides an improved orientation information to a user.

It is a further object of the present invention to provide an improved method for mapping of action potential data.

These and other objects of the present invention are accomplished by a medical system for mapping of action potential data with the features of claim 1. An inventive medical system for mapping of action potential data comprises an elongated medical mapping device suitable for intravascular insertion having an electrode assembly located at a distal portion of the mapping device, a data processing and control unit for processing data received from the mapping device, the data processing and control unit including a heart model generator for visualizing a 3-dimensional heart model based on one of electrical navigation system, MRI or CT scan data of a heart, a display unit for simultaneously displaying both the 3-dimensional heart model visualization and the processed data of the mapping device in form of a model visualization (40) of action potential data. The heart model generator is configured to structure 3D scan data of the heart into the six directions a, b, c, d, e and f of a cube, each direction is associated with a separate Cartesian coordinate system with $X^{(a,b,c,d,e \text{ or } f)}$, $Y^{(a,b,c,d,e \text{ or } f)}$, $Z^{(a,b,c,d,e \text{ or } f)}$ coordinates, wherein for assigning each 3D scan data point to one of the six directions a, b, c, d, e or f the following 6 true or false tests are applied:

$$(X_{max}^{(a)}-|X_{mes}^{(a)}|)>Z_{mes}^{(a)} \wedge (Y_{max}^{(a)}-|Y_{mes}^{(a)}|)>Z_{mes}^{(a)}$$

$$(X_{max}^{(b)}-|X_{mes}^{(b)}|)>Z_{mes}^{(b)} \wedge (Y_{max}^{(b)}-|Y_{mes}^{(b)}|)>Z_{mes}^{(b)}$$

$$(X_{max}^{(c)}-|X_{mes}^{(c)}|)>Z_{mes}^{(c)} \wedge (Y_{max}^{(c)}-|Y_{mes}^{(c)}|)>Z_{mes}^{(c)}$$

$$(X_{max}^{(d)}-|X_{mes}^{(d)}|)>Z_{mes}^{(d)} \wedge (Y_{max}^{(d)}-|Y_{mes}^{(d)}|)>Z_{mes}^{(d)}$$

$$(X_{max}^{(e)}-|X_{mes}^{(e)}|)>Z_{mes}^{(e)} \wedge (Y_{max}^{(e)}-|Y_{mes}^{(e)}|)>Z_{mes}^{(e)}$$

$$(X_{max}^{(f)}-|X_{mes}^{(f)}|)>Z_{mes}^{(f)} \wedge (Y_{max}^{(f)}-|Y_{mes}^{(f)}|)>Z_{mes}^{(f)}$$

wherein max indicates the maximum leg length of the respective X, Y or Z axis and wherein mes indicates the measured value of a scanned data point, and wherein the data point is assigned to the direction a, b, c, d, e or f for which the test outcome is true.

With this improved medical system, the wildly scattered 3D coordinates from either one of an electrical navigation system, of a CT or of an MRI scan as generated by a classical 3D engine are transformed in a system of six directions, which is similar to an anatomical coordinate system. The data are structured into the six directions which correspond to anatomical directions such as left, right, ventral, dorsal, rostral (top), and caudal (bottom) exactly defined in the anatomical space. With the six directions available, orientation in the 3D model visualization is improved in that the person using the medical system can navigate intuitively through the 3D model. Accordingly, the inventive medical system allows for repetitive identification of locations with different instruments such as mapping catheters and ablation catheters.

Advantageously, if for a given X, Y coordinate of a direction a, b, c, d, e or f more than one Z coordinate value exist, only the highest Z value will be indexed for being displayed on the display unit so that a simply structured model may be generated.

In an advantageous embodiment of the present invention, the six directions a, b, c, d, e and f of the cube originate from a centrum, wherein each possible viewing direction in the visualization of the 3-dimensional heart model on the display unit passes the centrum, and wherein the centrum defines for each viewing direction a plane which passes the centrum and which intersects a respective viewing direction perpendicularly, and wherein the heart model generator only visualizes data points on the display unit that are located in viewing direction behind the plane. By excluding the data points that are located in viewing direction in front of the plane, disturbing foreground structure is removed from the 3D model to provide a clear and un-disturbed view on the background structures.

Preferably, in a further embodiment of the present invention, each area of the 3-dimensional heart model visualization associated with a cube direction a, b, c, d, e or f carries an indicator chosen from one of a color and a pattern, the indicator being characteristic for the cube direction a, b, c, d, e or f associated to the area. With these indicators, orientation of a user in the model is improved.

In a further favorable embodiment, the indicator increases in intensity, especially in one of color intensity and pattern filling grade, in the viewing direction. E.g. the color may change from a light color adjacent or close to the plane to a darker color in a distance to the plane.

If the indicator is a pattern, then the pattern may change from slightly filled adjacent or close to the plane to greatly filled in a distance to the plane. By means of this increasing intensity in filling grade or color intensity, the user may intuitively obtain an even more improved spatial orientation within the 3D model.

Advantageously, the 3-dimensional heart model visualization includes a model visualization of an electrode assembly, especially of a mapping catheter head. By means of integrating a model visualization of the electrode assembly and/or of the catheter head, the user may easily identify the location where the electrode assembly or the catheter head is located at a given point in time and may follow all its movements within the 3D heart model visualization.

Further, it may be advantageous to include a model visualization of action potential data in the 3-dimensional heart model visualization. By including the action potential data in the 3-dimensional heart model visualization, anomalies such as circular excitation patterns ("rotors") may easily be identified by a user of the system and being spatially localized in the 3D heart model and may easily be spatially associated to the visualization of the electrode assembly or catheter head. The position and extent of the anomalies like the "rotors" in the 3D heart model may be memorized and being stored in a memory of the medical system. Accordingly work with the 3D model visualization could be interrupted and data being reloaded to the 3D model generator upon resuming a session. Such interruptions may occur e.g. when the catheter used with the medical system is changed. E.g. when a mapping catheter is replaced by an ablation catheter.

It should be mentioned that even though a 3D heart model visualization is discussed in respect to the inventive medical system, the system may also be used to visualize other anatomic areas of a human or animal body.

In an advantageous embodiment of the present invention, the electrode assembly on the mapping catheter or elongated medical device is formed in a spiral configuration with at least two spiral arms, preferentially 2 to 30, preferentially 2 to 22, more preferentially 2 to 14. The advantage of this arrangement is that the density of electrodes can easily be increased without the need to provide a longer storage area at the elongated medical device for storing the electrode assembly in the unexpanded condition of the support arms when arranged closely along a portion of the elongated body.

Alternatively, the electrode assembly may be configured in a spherical or spherical grid-like configuration comprising electrode carrying bows that are arranged in a longitudinal and/or latitudinal direction. Further alternatively, electrodes may be arranged on an expandable balloon type carrier.

An advantageous method for mapping of action potential data comprising the steps of obtaining 3D scan data consisting of a multitude of individual 3D scan data points of a heart from on one of an electrical navigation system, MRI or CT, structuring the 3D scan data of the heart into six directions a, b, c, d and f of a cube, wherein each direction is associated with a separate Cartesian coordinate system with $X^{(a,b,c,d,e \text{ or } f)}$, $Y^{(a,b,c,d,e \text{ or } f)}$, $Z^{(a,b,c,d,e \text{ or } f)}$ coordinates, applying the following six true or false tests to each of the scan data points for associating each 3D scan data point to one of the six directions a, b, c, d, e or f:

$$(X_{max}^{(a)} - |X_{mes}^{(a)}|) > Z_{mes}^{(a)} \wedge (Y_{max}^{(a)} - |Y_{mes}^{(a)}|) > Z_{mes}^{(a)}$$

$$(X_{max}^{(b)} - |X_{mes}^{(b)}|) > Z_{mes}^{(b)} \wedge (Y_{max}^{(b)} - |Y_{mes}^{(b)}|) > Z_{mes}^{(b)}$$

$$(X_{max}^{(c)} - |X_{mes}^{(c)}|) > Z_{mes}^{(c)} \wedge (Y_{max}^{(c)} - |Y_{mes}^{(c)}|) > Z_{mes}^{(c)}$$

$$(X_{max}^{(d)} - |X_{mes}^{(d)}|) > Z_{mes}^{(d)} \wedge (Y_{max}^{(d)} - |Y_{mes}^{(d)}|) > Z_{mes}^{(d)}$$

$$(X_{max}^{(e)} - |X_{mes}^{(e)}|) > Z_{mes}^{(e)} \wedge (Y_{max}^{(e)} - |Y_{mes}^{(e)}|) > Z_{mes}^{(e)}$$

$$(X_{max}^{(f)} - |X_{mes}^{(f)}|) > Z_{mes}^{(f)} \wedge (Y_{max}^{(f)} - |Y_{mes}^{(f)}|) > Z_{mes}^{(f)}$$

wherein max indicates the maximum leg length of the respective X, Y or Z axis and wherein mes indicates the measured value of a scanned data point, and wherein each of the data points is then assigned to the direction a, b, c, d, e or f for which the test outcome is true, and displaying the 3-dimensional heart model in a visualization on a display unit.

With this improved method, the wildly scattered 3D coordinates from either one of an electrical navigation system, of a CT or of an MRI scan as generated by a classical 3D engine are transformed in a system of six directions, which is similar to an anatomical coordinate system. The data are structured into the six directions which correspond to anatomical directions such as left, right, ventral, dorsal, rostral (top), and caudal (bottom) exactly defined in the anatomical space. With the six directions available, orientation in the 3D model visualization is improved in that the person using the medical system can navigate intuitively through the 3D model. Accordingly, the inventive medical system allows for repetitive identification of locations with different instruments such as mapping catheters and ablation catheters.

In a further advantageous step, action potential data are measured by means of an electrode assembly located at a distal portion of a mapping device and are processed in a control unit, and further, the processed data of the mapping device in form of a model visualization of action potential data and the 3-dimensional heart model are both simultaneously displayed in a single visualization on the display unit. Hence, action potential data including anomalies such as circular excitation patterns ("rotors") may easily be identified by a user of the system and being spatially localized in the 3D heart model and may easily be spatially associated to the visualization of the electrode assembly or catheter head. The position and extent of the anomalies like the "rotors" in the 3D heart model may be memorized and being stored in a memory of the medical system. Accordingly, work with the 3D model visualization could be interrupted and data being reloaded to the 3D model generator upon resuming a session. Such interruptions may occur e.g. when the catheter used with the medical system is changed. E.g. when a mapping catheter is replaced by an ablation catheter.

In an advantageous embodiment of the inventive method, if for a given X, Y coordinate of a direction a, b, c, d, e or f more than one Z coordinate value exist, only the highest Z value will be indexed for being displayed on the display unit, so that a simply structured model may be generated.

In a further inventive embodiment of the method, the six directions a, b, c, d, e and f of the cube originate from a centrum, wherein each possible viewing direction in the visualization of the 3-dimensional heart model on the display unit passes the centrum, and wherein the centrum defines for each viewing direction a plane which crosses the centrum and which intersects the respective viewing direction perpendicularly, and wherein only those data points are visualized on the display unit that are located in viewing direction behind the plane. By excluding the data points that are located in viewing direction in front of the plane, disturbing foreground structure is removed from the 3D model to provide a clear and undisturbed view on the background structures.

Advantageously each area of the 3-dimensional heart model visualization associated with a cube direction a, b, c, d, e or f is marked with an indicator which is one of a color and a pattern, the indicator being characteristic for the cube direction a, b, c, d, e or f associated to the area. With these indicators, orientation of a user in the model is improved.

In a further advantageous step, the intensity of the indicator may be increased, especially in one of color intensity and pattern filling grade, in the viewing direction. With this increase intensity in filling grade or color intensity, the user may intuitively obtain an even more improved spatial orientation within the 3D model.

A model visualization of an electrode assembly is displayed on the display unit together with the 3-dimensional heart model visualization. By including the action potential data in the 3-dimensional heart model visualization, anomalies such as circular excitation patterns ("rotors") may easily be identified by a user of the system and being spatially localized in the 3D heart model and may easily be spatially associated to the visualization of the electrode assembly or catheter head. The position and extent of the anomalies like the "rotors" in the 3D heart model may be memorized and being stored in a memory of the medical system. Accordingly, work with the 3D model visualization could be interrupted and data being reloaded to the 3D model generator upon resuming a session. Such interruptions may occur e.g. when the catheter used with the medical system is changed. E.g. when a mapping catheter is replaced by an ablation catheter.

Further features of the invention, its nature and various advantages will become more apparent from the accompanying drawings and the following detailed description of the preferred embodiments, in which:

DETAILED DESCRIPTION

The present invention is directed to a medical system for mapping of action potential data comprising an elongated medical device 1 suitable for intravascular insertion, such as a catheter for exploration or treatment of a vessel, organ or other body cavity which includes an electrode assembly for electro-anatomic mapping of cardiac or vessel areas or the like medical apparatus. The elongated medical device 1 may have a force sensor which could be formed as a 3D optical force sensor with which contact forces between a distal portion of the medical device and a wall of the vessel, organ or other body cavity can be measured in three dimensions. Such an optical force sensor is e.g. disclosed in the parallel patent application PCT/EP2015/001097 (herewith incorporated by reference). In operation of the medical device, the force sensing ability may be used periodically to measure the contact forces at certain points, or, alternatively, it may be used to continuously monitor such contact forces to support the operation of the medical device. The electrode assembly may be used to map circular excitation patterns (rotors), e.g. of the left atrium of the heart, as will be described in more detail in the following.

Referring to FIGS. 1 to 4a, a medical system for mapping of action potential data comprises an elongated medical device 1 which is formed as a mapping catheter, e.g. to be used in the curative treatment of Atrial Fibrillation and other hearth rhythm diseases like Atrial Flutter, Accessory Pathways or Ventricular Tachycardia. The mapping catheter may also include the functionality of an ablation catheter. The elongated medical device 1 comprises an elongated body 2, which is only partly shown in FIGS. 1 and 2. At a distal portion 3 of the elongated medical device 1, there may be a tip electrode arranged at its distal end 4 and a ground electrode may be arranged at the distal portion 3 of the elongated body 2 in case an ablation functionality is included in the device.

Figure 4:
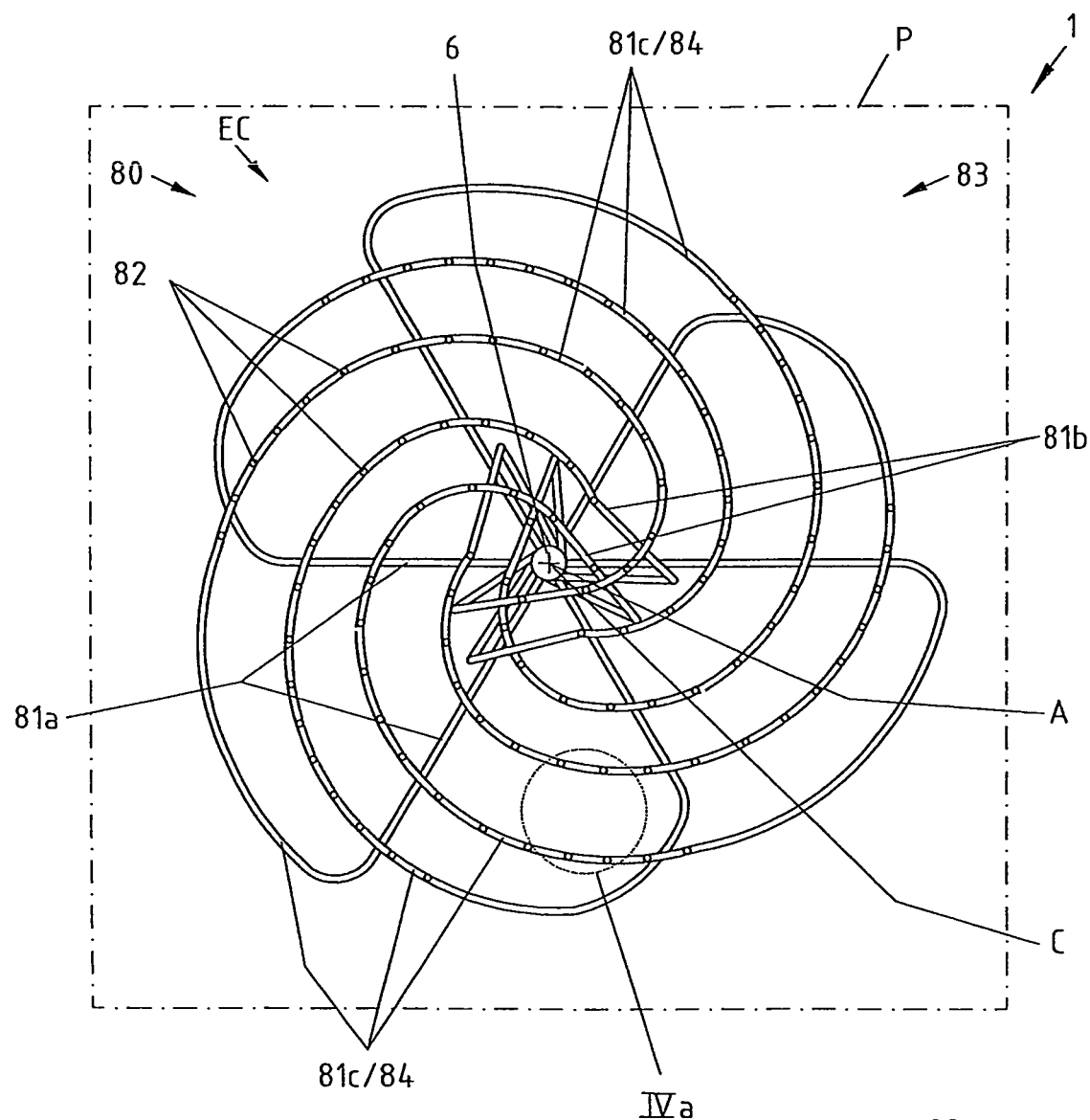
FIG. 4 is a top view of the elongated medical device according to FIG. 2 in the second, expanded condition of the electrode assembly.

The elongated medical device 1 may comprise a fluid supply line 13, which may be connected to a fluid supply 17 (see FIG. 4). This fluid supply line 13 is in fluid-guiding connection to at least one fluid opening in the tip electrode 6, through which an irrigation fluid, like e.g. a saline fluid, may flow to the outside of the distal portion 3 of the elongated medical device 1 to irrigate a surrounding portion of the vessel, organ or other body cavity into which the elongated medical device 1 has been introduced. Fluid flow may be controlled by the handle 7 or by a control at the fluid supply 17. Irrigation fluid will be distributed especially during or after an electro-ablation procedure has been performed.

The distal portion may house towards its distal end 4 a force sensor assembly/force sensor, preferably an optical force sensor such as described in co-pending patent application PCT/EP2015/001097 of the applicant.

At the proximate end of the elongated medical device 1 a handle 7 is disposed which comprises a first handle part 7a and a second handle part 7b. Via the handle 7 electro-ablation may be initiated (if this functionality is available) and also the operation of an electrode assembly 80/mapping electrode assembly may be controlled.

The electrode assembly 80/mapping electrode assembly is located at the distal portion 3 and comprises in the embodiment of FIGS. 1-4a six support arms 81. Each support arm 81 has a proximal part 81a, a distal part 81b and a central part 81c between the proximal part 81a and the distal part 81b. Generally, 2-32 spiral arms may be realized, each arm carrying a number of e.g. 8 to 30 electrodes.

The distal parts 81b of each of the support arms 81 are attached to the distal portion 3 adjacent to its distal end 4 and the proximal parts 81a of the support arms 81 are coupled to a steering member 25 located on an end of the proximal portion 5 that faces the distal portion 3.

Figure 1:
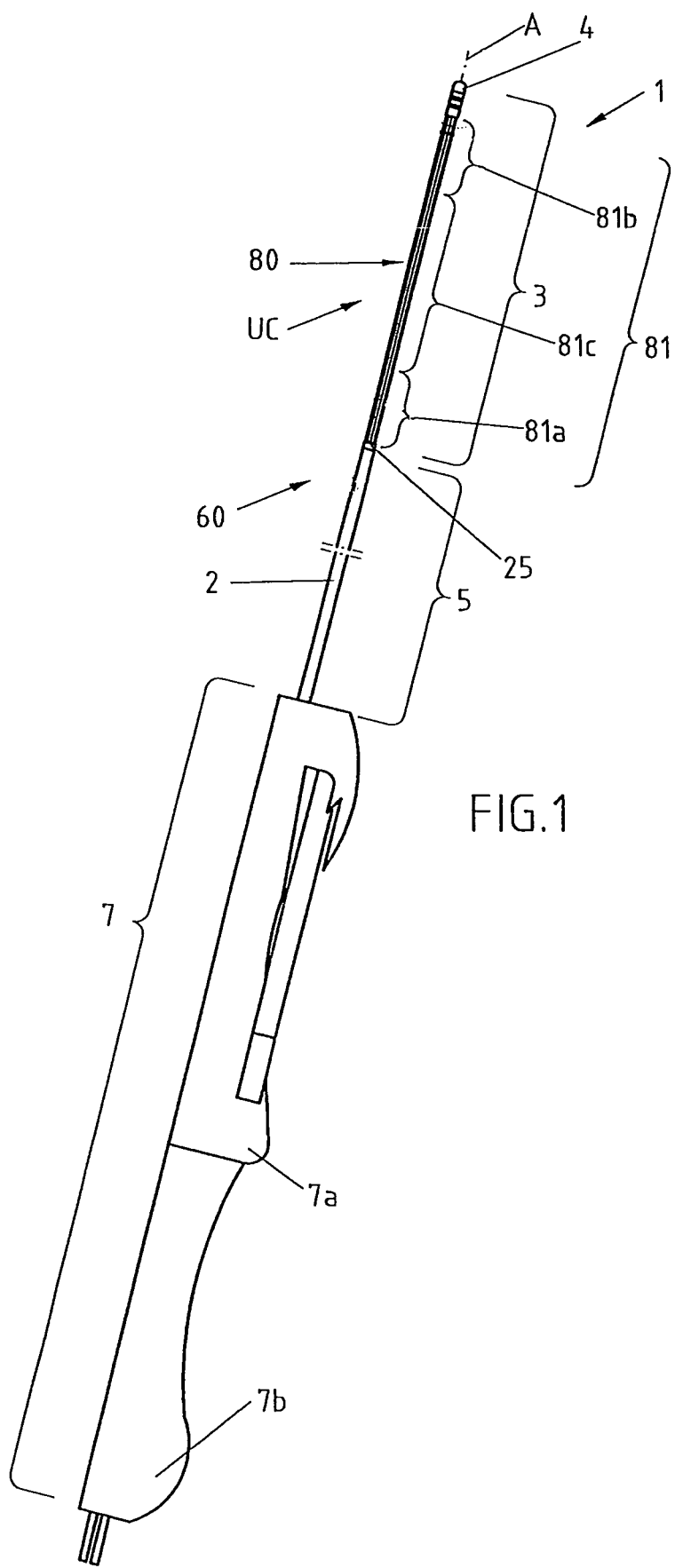
FIG. 1 is a schematic view of a medical system for mapping of action potential data, comprising an elongated medical device in form of a catheter for exploration or treatment of a vessel or organ or other body cavity which includes an electrode assembly for electro-anatomic mapping of cardiac or vessel areas in a first, unexpanded condition of the electrode assembly.

The support arms 81 are configured to have a first, unexpanded condition UC, in which the support arms 81 are arranged in a close fit along a portion of the elongated body 2, as is best seen in FIG. 1. In this unexpanded condition UC of the support arms 81 the steering member 25 is located in its first position 60, remote, or in other words in a maximum distance to the distal end 4.

Figure 2:
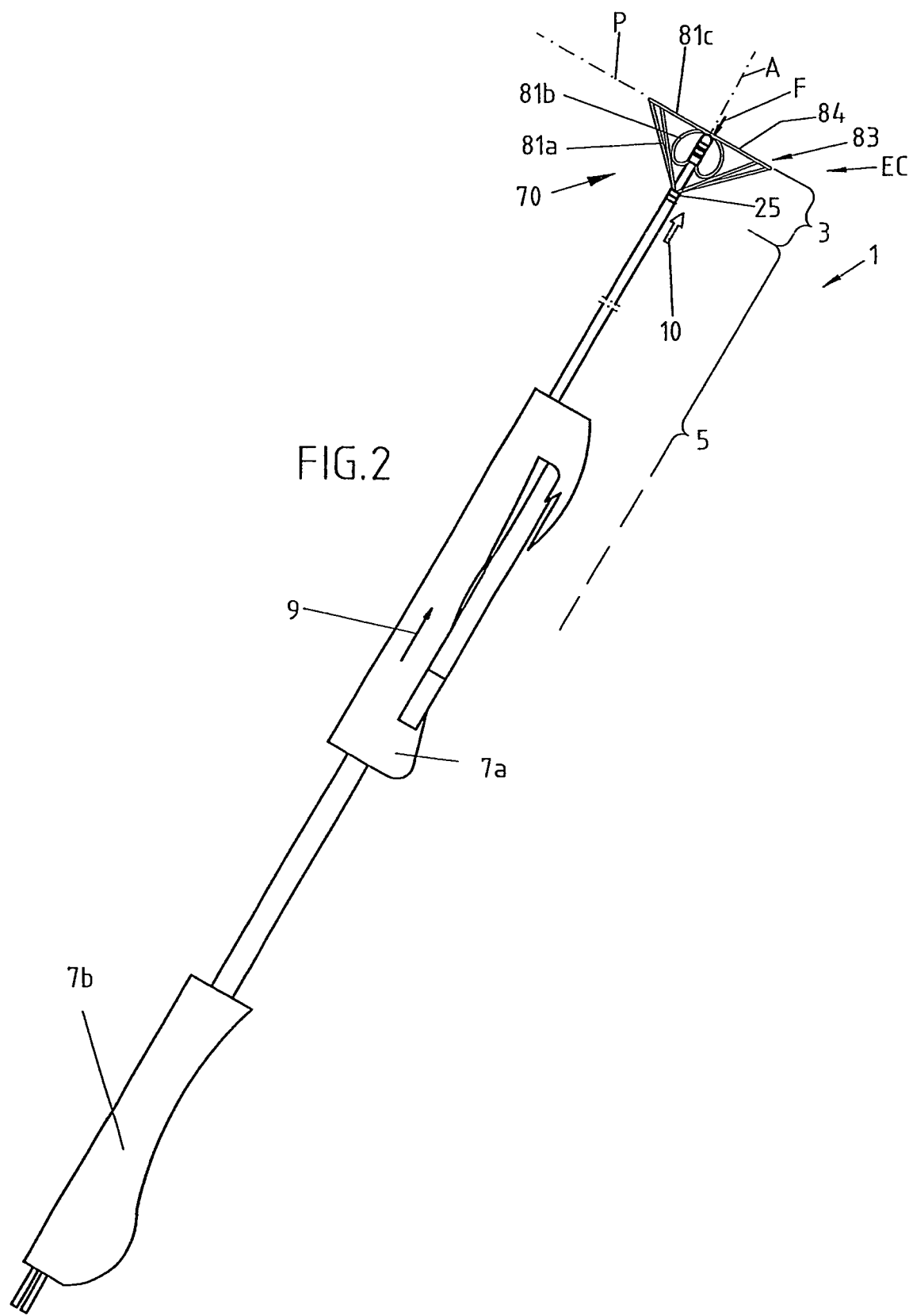
FIG. 2 is a schematic view of the medical system for mapping of action potential data, comprising an elongated medical device of FIG. 1 in a second, expanded condition of the electrode assembly.
Figure 4A:
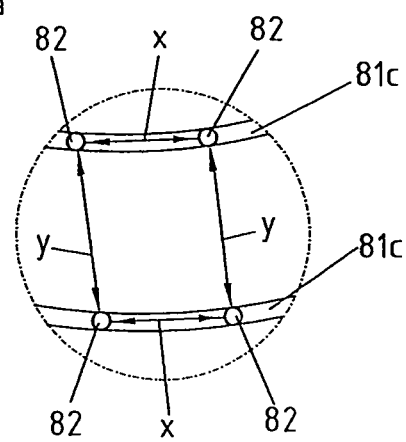
FIG. 4a is an enlarged view of an area of the electrode assembly of the elongated medical device of FIG. 6 according to the marking IVa in FIG. 4.

With reference to FIGS. 2 and 4-4a, the support arms 81 are further configured to have a second, expanded condition EC, in which the central parts 81c of each of the support arms 81 project away from the elongated body 2 and are spirally wound, forming a spiral structure 83 with eight spiral arms 84 and the distal end 4 being located in a center of symmetry C of the spiral structure 83. Spiral arms 84 essentially correspond to the central parts 81c of the support arms. The center of symmetry C of the spiral structure 83 lies in a longitudinal axis A which is defined by the distal portion 3 of the elongated medical device 1. In this second, expanded condition EC of the support arms 81 the steering member 25 located in its second position 70, nearby, or in other words in a minimum distance to the distal end 4. The spiral structure 83 with the spiral arms on the other hand define a plane P which intersects the longitudinal axis A essentially perpendicularly. Further, in this expanded condition EC of the support arms 81 the electrode assembly forms an electrode array of a plurality of electrodes 81 arranged essentially in the plane P. The electrode array in the present embodiment comprises 6 support arms 81 with each support arm carrying 18 electrodes so that the electrode array counts 6 times 18 electrodes summing up to a total of 108 electrodes and has a size of about 4.4 cm in diameter which is about 15.2 $cm^2$. The corresponding spatial resolution is about 10 times higher than that of existing electro-mapping technologies.

According to FIG. 4a, two adjacent electrodes 82 on an individual support arm 81 are arranged in a distance x to each other. This distance x is between 2 mm to 9 mm, preferably between 2.5 mm to 4.5 mm. Further, two adjacent electrodes 82 on two adjacent support arms 81 are arranged in a distance y to each other. This distance y is between 2 mm to 9 mm, preferentially between 2.5 mm to 4.5 mm. Distances x and y are correlated with each other in that the distance x and the distance y are equal within a maximum tolerance in a range of +/−0.5 mm.

By means of the handle 7a, which may be moved away from the second handle part 7b (see movement of first handle part 7a indicated by arrow 9 in FIG. 2), the annular steering member 25 can be moved from its first position 60 towards the distal end 4 of the elongated medical device 1 into its second position 70 (see movement of annular steering member 25 indicated by arrow 10 in FIG. 2), reducing the distance between the annular steering member 25 and the distal end 4. With such movement of the annular steering member 25 the electrode assembly 8/mapping electrode assembly and their six support arms 81 will be transferred from their unexpanded condition UC to their expanded condition EC, opening and expanding the spiral structure 83 of the electrode assembly 81. In this expanded condition EC the electrode assembly is ready for use in mapping circular excitation patterns (rotors), e.g. of the left atrium of the heart. Of course, a movement of the first handle part 7a in the other direction back towards the second handle part 7b, will close and collapse the spiral structure 83 of the electrode assembly 81, transferring it to the unexpanded condition EC of the electrode assembly 80/mapping electrode assembly and their eight support arms 81.

The central part 81c of each support arm 81 carries a plurality of electrodes 82 (also referenced to as mapping electrodes) which are gold-plated for enhanced electro-conductability. In the present embodiment there are eighteen electrodes 82 disposed on each support arm. The surface size of an electrode 82 is between 0.01 mm² and 0.25 mm².

It should be mentioned that instead of a spiral configuration, the electrode assembly may be configured in a spherical or spherical grid-like configuration comprising electrode carrying arms that are arranged in a longitudinal and/or latitudinal direction. Further, electrodes may be arranged on an expandable balloon type carrier instead of carrying arms.

The medical system comprises an electronic unit (not shown) which is arranged within the elongated medical device 1. In an alternate embodiment, the electronic unit may be arranged external to the elongated medical device 1. The electronic unit is adapted to process and digitize analog signals received from the electrodes 82.

The electronic unit may comprise operational amplifiers which acquire AC inputs from the electrodes 82. Signals received may be low pass filtered at 200 Hz and read by an analog multiplexer and through a 14 bit analog-digital converter and forwarded into a serial LVDS digital output signal.

Figure 3:
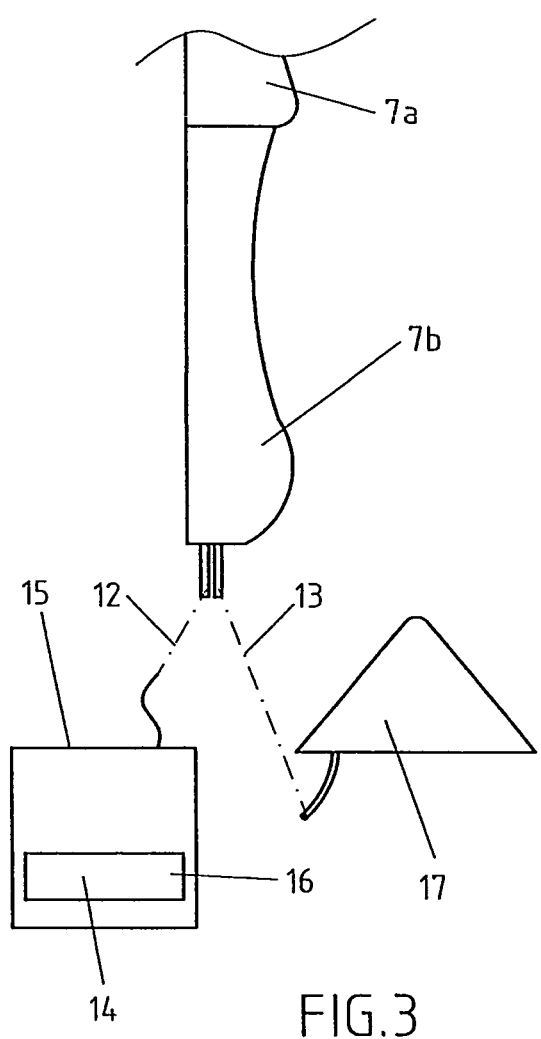
FIG. 3 is an enlarged view of a proximal end area of the proximal portion of the elongated medical device of FIG. 1 connected to a data processing and control unit/data output unit of the medical system.

The electrode assembly 80 and the associated electronics unit is connected via a line 12 with a data processing and control unit 15 (see FIG. 3). The data processing and control unit 15 processes electrode mapping data from the electrode assembly and outputs mapping data via a data output unit 16. It may also process sensor data received from a force sensor. Line 12 may be a ribbon cable, flat conductor, flat flexible cable or the like.

The data processing and control unit 15 may be formed as a standard personal computer and the elongated medical device 1 respectively the catheter system has an interface to a standard computer which is connected to all the electronic components.

In respect to the mapping data, the data processing and control unit 15 is configured to process digitized electrode measurement data and to output data for visualizing circular excitation pattern (rotors) e.g. in the left atrium of a patient's heart on a data output unit/display unit 16 which will be explained in detail with respect to FIG. 7.

In electro-anatomical mapping systems the excitation in response to a pacing stimulus is measured while travelling along the walls of the atrium. The path from one side to the other is around 6 cm and the excitation needs 200 ms for this distance. In rotors, the "eye of the storm" has a diameter of around 1 cm (circumference of 3 cm). Thus rotor excitation cycles have a period of 200 ms or 300 beats per minute. Since action potentials are about 100 ms in duration excitation clusters have a size of about 1.5 cm.

Figure 7:
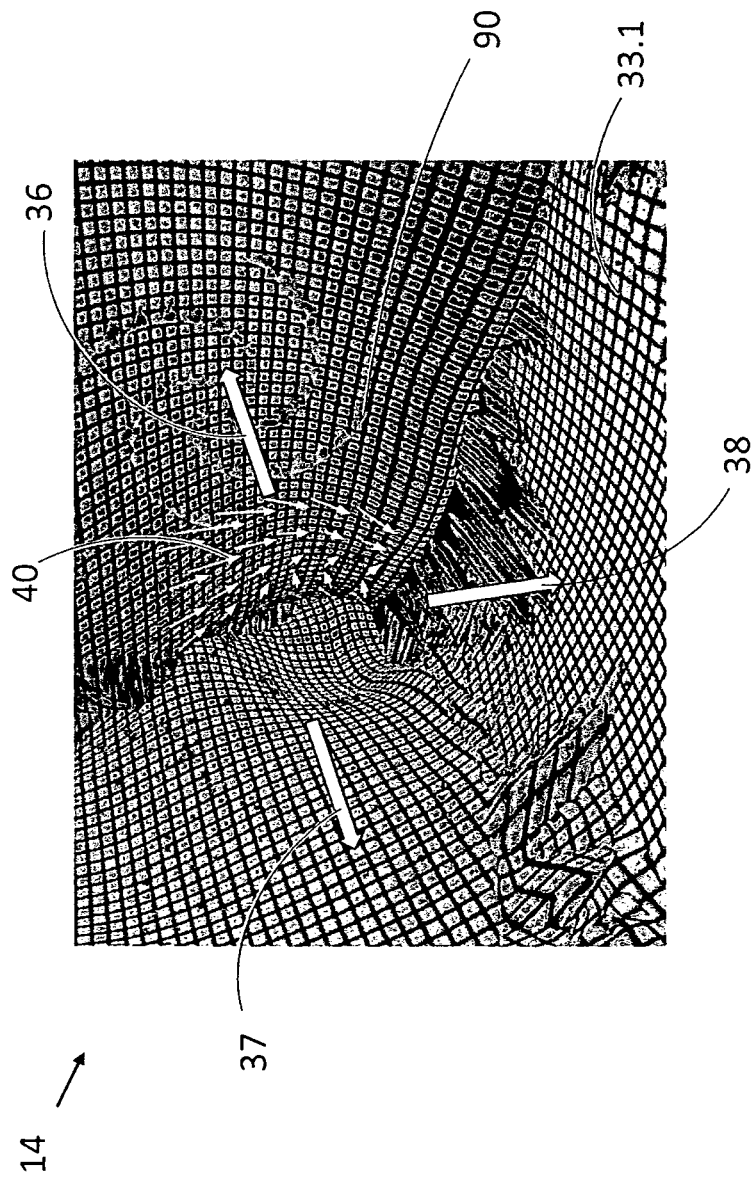
FIG. 7 is a representation of an exemplary visual output on the screen of the display unit.

In FIG. 7, the screen 14 of the display unit 16 shows a 3D heart model visualization according to the present invention. For example the tissue of the left atrium of the heart may be displayed as a 3D model visualization. To generate such a visualization, the data processing and control unit 15 includes a model generator for visualizing a 3-dimensional heart model based on primary 3D scan data derived from an electrical navigation system, MRI or CT scan of a heart.

Figure 5A:
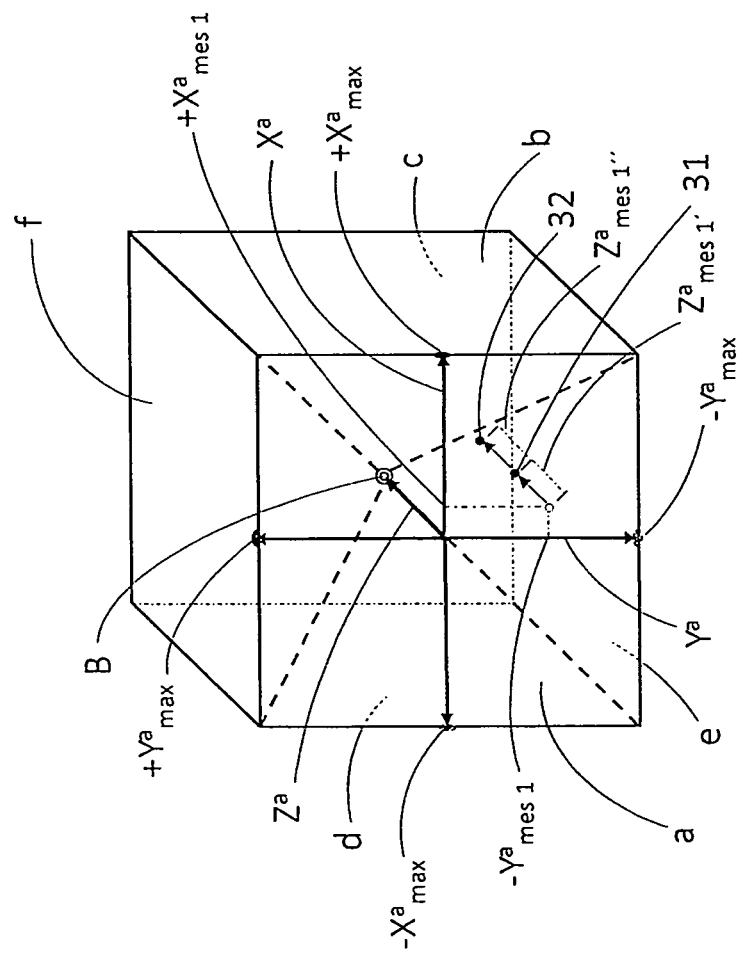
FIG. 5a is a representation of the three dimensional model space used for structuring of 3D scan data of e.g. the heart in a first orientation.
Figure 5B:
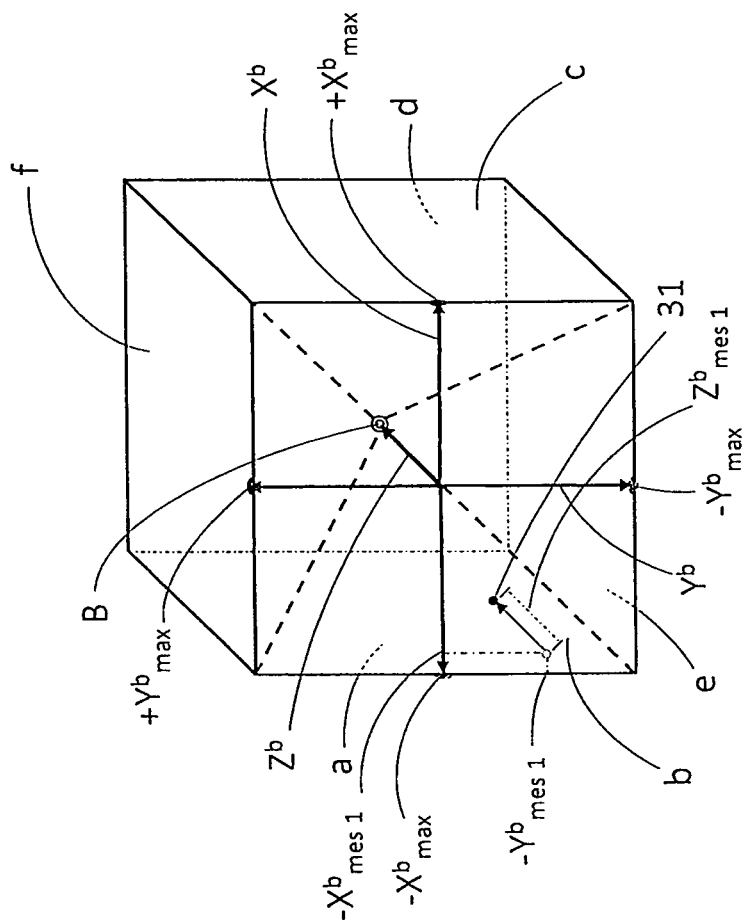
FIG. 5b is the representation of the three dimensional model space used for structuring of 3D scan data in a second orientation.

With reference to FIGS. 5a and 5b the heart model generator is configured to structure 3D scan data of the heart into six directions a, b, c, d, e and f of a cube. Each direction is associated with a separate Cartesian coordinate system with $X^{(a,b,c,d,e\ or\ f)}$, $Y^{(a,b,c,d,e\ or\ f)}$, $Z^{(a,b,c,d,e\ or\ f)}$ coordinates, wherein for assigning each 3D scan data point to one of the six directions a, b, c, d, e or f the following six true or false tests are applied by heart model generator, respectively the data processing and control unit 15:

$$(X_{max}^{(a)} - |X_{mes}^{(a)}|) > Z_{mes}^{(a)} \wedge (Y_{max}^{(a)} - |Y_{mes}^{(a)}|) > Z_{mes}^{(a)}$$

$$(X_{max}^{(b)} - |X_{mes}^{(b)}|) > Z_{mes}^{(b)} \wedge (Y_{max}^{(b)} - |Y_{mes}^{(b)}|) > Z_{mes}^{(b)}$$

$$(X_{max}^{(c)} - |X_{mes}^{(c)}|) > Z_{mes}^{(c)} \wedge (Y_{max}^{(c)} - |Y_{mes}^{(c)}|) > Z_{mes}^{(c)}$$

$$(X_{max}^{(d)} - |X_{mes}^{(d)}|) > Z_{mes}^{(d)} \wedge (Y_{max}^{(d)} - |Y_{mes}^{(d)}|) > Z_{mes}^{(d)}$$

$$(X_{max}^{(e)} - |X_{mes}^{(e)}|) > Z_{mes}^{(e)} \wedge (Y_{max}^{(e)} - |Y_{mes}^{(e)}|) > Z_{mes}^{(e)}$$

$$(X_{max}^{(e)} - |X_{mes}^{(f)}|) > Z_{mes}^{(f)} \wedge (Y_{max}^{(f)} - |Y_{mes}^{(f)}|) > Z_{mes}^{(f)}$$

In these test formulas, the term "max" indicates the maximum leg length of the respective X, Y or Z axis and the term "mes" indicates the measured value of a scanned data point. According to the test results, each individual data point is then assigned by the heart model generator/data processing and control unit 15 to that direction a, b, c, d, e or f for which the test outcome has the value "true". In FIGS. 5a and 5b spatial relation of the directions a, b, c, d, e or f of the cube is visualized from two different perspectives, with direction a in front (FIG. 5a) and with direction b in front (FIG. 5b). As an example two data points, a first 31 and a second 32 are shown in FIG. 5a. The projection 30 of these data points 31, 32 on the $-Y^a$-+$X^a$ plane of direction a define the $-Y^a_{mes}$ and $+X^a_{mes}$ values. The respective distance of data points 31, 32 along $Z^a$ direction towards the centrum B of defines the $Z^a$ value.

In this example the 3D scan data of the first data point 31 have the following values:

$$+X^a_{mes} = 0.54$$

$$-Y^a_{mes} = 1.64 \text{ and}$$

$$Z^a_{mes} = 0.27$$

with $X^a_{max} = 3$ and with $Y^a_{max} = 3$; ($X^a_{max}$ and $Y^a_{max}$ are predefined by the model generator)

The test for direction a will be as follows:

$$(X_{max}^{(a)} - |X_{mes}^{(a)}|) > Z_{mes}^{(a)} \wedge (Y_{max}^{(a)} - |Y_{mes}^{(a)}|) > Z_{mes}^{(a)}$$

with numbers added:

$$(3 - |0.54|) > 0.27 \wedge (3 - |-1.64|) > 0.27$$

$$(2,46) > 0.27 \wedge (1.36) > 0.27$$

So the result has the value true and hence first data point 31 will be assigned to the direction a.

In this example the 3D scan data of the second data point 32 have the following values:

$$+X^a_{mes} = 0.54$$

$-Y^a_{mes}=-1.64$ and $Z^a_{mes}=0.6$ with $X^a_{max}=3$ and with $Y^a_{max}=3$; ($X^a_{max}$ and $Y^a_{max}$ are predefined by the model generator)

The test for direction a will be as follows:

$(X_{max}^{(a)}-|X_{mes}^{(a)}|)>Z_{mes}^{(a)}\wedge(Y_{max}^{(a)}-|Y_{mes}^{(a)}|)>Z_{mes}^{(a)}$ with numbers added:

$(3-|0.54|)>0.6\wedge(3-|-1.64|)>0.6$ $(2,46)>0.6\wedge(1.36)>0.6$

So the result has the value "true" and hence the second data point 32 will be assigned to the direction a.

In case that for a given X, Y coordinate of a direction a, b, c, d, e or f more than one Z coordinate value exist, only the highest Z value will be indexed for being displayed on the display unit 16. In the example provided above, this means that only the second data point 32 with the value $Z^a=0.6$ will be indexed by the model generator for being displayed and hence only this second data point 32 will be included in the data provided by the model generator of the data processing and control unit 15 for the 3D model visualization to be displayed on the data output unit 16/monitor display.

Figure 6:
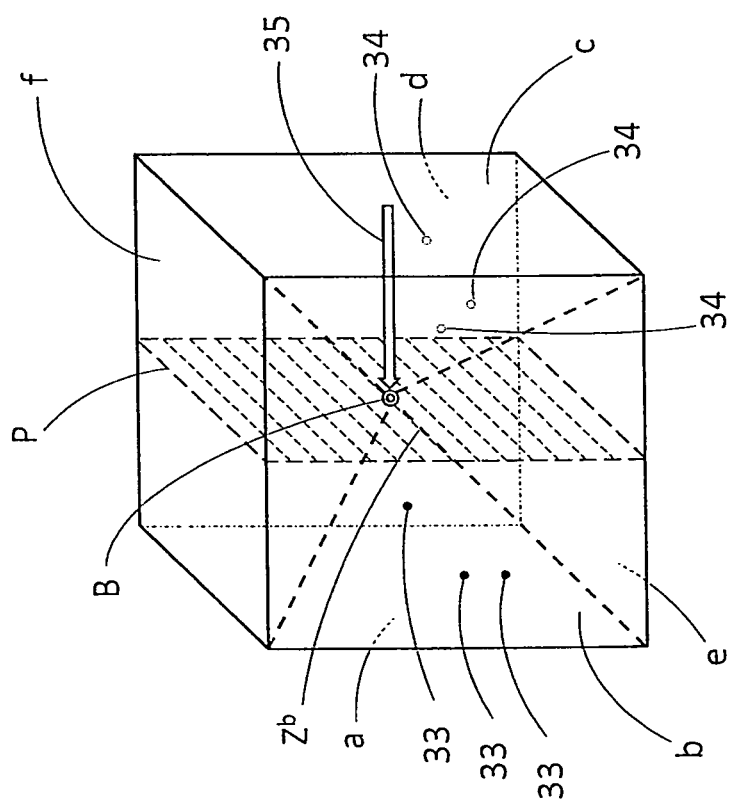
FIG. 6 is the representation of the three dimensional model space used for structuring of 3D scan data according to FIG. 5a with different information added.

With respect to FIGS. 5a, 5b and 6 the six directions a, b, c, d, e and f of the cube originate from a centrum B and as can be seen in FIG. 6 each possible viewing direction 35 in the visualization of the 3-dimensional heart model passes this centrum B. The centrum B thereby defines for each viewing direction 35 a plane P which passes the centrum B and which intersects a respective viewing direction 35 perpendicularly.

As can be seen in FIG. 6, the model generator only visualizes data points 33 on the display unit 16 that are located in viewing direction 35 behind the plane P. Data points 34 that are located in the viewing direction 35 in front of plane P are not visualized by the model generator and are hence not displayed on the data output unit 16/monitor display.

Referring again to FIG. 7, The data output screen 14 of the display unit 16 will display in operation a 3D model visualization of an organ, such as the heart. The respective excitation pattern map is put on the surface of this 3D model visualization as a texture of electro-anatomic data arrows 40. In the example of FIG. 7 the viewing direction is vertical to the image plane and arrows 36, 37 and 38 indicate an information on the directions of the cube ($3^{rd}$ to $5^{th}$ directions of the cube are indicated) or the respective anatomical directions. Data points 33.1 are displayed in form of junctions of a grid of squares which are filled with a grey-scale coloring where intense color indicates areas or spots remote from the centrum and brighter color indicates areas closer to the centrum. Areas of the 3D model visualization made up by groups of data points associated to one of the different directions (36, 37, 38) differ in color fill grade from the other areas made up by respective other groups of data points associated to the respective other direction (37, 38, 36). A visualization 90 of the electrode assembly is also included in the 3D model as a different texture. The visualization 90 is always shown in the model at its current location within the vessel or organ, e.g. the heart, so that the user has a good orientation.

REFERENCE LIST 1 elongated medical device
2 elongated body
3 distal portion
4 distal end
5 proximal portion
7 handle
7a first handle part
7b second handle part
9 arrow
10 direction
12 data line
13 fluid supply line
14 sub-zone of data output screen/data output screen
15 data processing and control unit
16 data output unit/display unit
17 fluid supply
25 steering member (axially movable)
30 projection (of a data point)
31 $1^{st}$ data point
32 $2^{nd}$ data point
33 data points
33.1 data points
34 data points
35 viewing direction
36 arrow (indicating $3^{rd}$ direction)
37 arrow (indicating $4^{th}$ direction)
38 arrow (indicating $5^{th}$ direction)
40 (electro-anatomic) data arrows/visualization
60 first position of 25
70 second position of 25
80 electrode assembly/mapping electrode assembly
81 support arms
81a proximal part
81b distal part
81c central part
82 electrodes/mapping electrodes
83 spiral structure
84 spiral arms
90 visualization of the electrode assembly
91 3-dimensional heart model visualization
A longitudinal axis
B centrum
C center of symmetry
EC expanded condition (of 80)
P plane
UC unexpanded condition (of 80)
X coordinate
Y coordinate
Z coordinate
a $1^{st}$ direction
b $2^{nd}$ direction
c $3^{rd}$ direction
d $4^{th}$ direction
e $5^{th}$ direction
f $6^{th}$ direction
x distance
y distance

The invention claimed is:

1. A medical system for mapping action potential data, comprising:
   an elongated medical mapping device suitable for intravascular insertion having an electrode assembly located at a distal portion of the mapping device;
   a data processing and control unit for processing data received from the mapping device, the data processing and control unit comprising a model generator for visualizing a 3-dimensional heart model based on one of an electrical navigation system, an MRI scan of a patient's heart, and a CT scan data of the patient's heart;
a display unit for simultaneously displaying both the 3-dimensional heart model and the processed data of the mapping device in a form of a model visualization of action potential data;
wherein the model generator is configured to structure 3D scan data of the heart into 6 directions a, b, c, d, e and f of a cube, each direction is associated with a separate Cartesian coordinate system with $X^{(a,b,c,d,e\ or\ f)}$, $Y^{(a,b,c,d,e\ or\ f)}$, $Z^{(a,b,c,d,e\ or\ f)}$ coordinates, and wherein each of the 3D scan data points is assigned to one of the 6 directions (a, b, c, d, e or f) and the following 6 true or false tests are applied:

$$(X_{max}^{(a)} - |X_{mes}^{(a)}|) > Z_{mes}^{(a)} \wedge (Y_{max}^{(a)} - |Y_{mes}^{(a)}|) > Z_{mes}^{(a)}$$

$$(X_{max}^{(b)} - |X_{mes}^{(b)}|) > Z_{mes}^{(b)} \wedge (Y_{max}^{(b)} - |Y_{mes}^{(b)}|) > Z_{mes}^{(b)}$$

$$(X_{max}^{(c)} - |X_{mes}^{(c)}|) > Z_{mes}^{(c)} \wedge (Y_{max}^{(c)} - |Y_{mes}^{(c)}|) > Z_{mes}^{(c)}$$

$$(X_{max}^{(d)} - |X_{mes}^{(d)}|) > Z_{mes}^{(d)} \wedge (Y_{max}^{(d)} - |Y_{mes}^{(d)}|) > Z_{mes}^{(d)}$$

$$(X_{max}^{(e)} - |X_{mes}^{(e)}|) > Z_{mes}^{(e)} \wedge (Y_{max}^{(e)} - |Y_{mes}^{(e)}|) > Z_{mes}^{(e)}$$

$$(X_{max}^{(f)} - |X_{mes}^{(f)}|) > Z_{mes}^{(f)} \wedge (Y_{max}^{(f)} - |Y_{mes}^{(f)}|) > Z_{mes}^{(f)}$$

wherein max indicates a maximum leg length for each of the respective X, Y and Z axes, mes indicates a measured value of a scanned data point, and each of the data points is assigned to the direction (a, b, c, d, e or f) for which the test outcome is true, and further wherein the 6 directions a, b, c, d, e and f of the cube originate from a centrum, wherein each viewing direction in the 3-dimensional heart model shown on the display unit passes through the centrum, and wherein the centrum defines for each viewing direction a plane which crosses the centrum and which intersects a respective viewing direction perpendicularly.

2. A medical system according to claim 1, wherein, if for a given X, Y coordinate of a direction (a, b, c, d, e or f) more than one Z coordinate value exists, only the highest Z value is indexed for being displayed on the data output unit.

3. A medical system according to claim 1, wherein the model generator is further configured only to visualize data points on the display unit that are located in the viewing direction behind the plane.

4. A medical system according to claim 1, wherein each area of the 3-dimensional heart model visualization associated with a cube direction (a, b, c, d, e or f) carries an indicator chosen from one of a color and a pattern, the indicator being characteristic for the cube direction (a, b, c, d, e or f) associated with each such area.

5. A medical system according to claim 4, wherein the indicator increases in intensity along the viewing direction.

6. A medical system according to claim 1, wherein the 3-dimensional heart model visualization includes a model visualization of an electrode assembly.

7. A medical system according to claim 1, wherein the 3-dimensional heart model visualization includes a model visualization of action potential data.

8. A method for mapping action potential data, comprising:
obtaining 3D scan data comprising a plurality of individual 3d scan data points corresponding to a patient's heart acquired using one of an electrical navigation system, an MRI scan, and a CT scan;
structuring the 3D scan data of the heart into 6 directions (a, b, c, d, e and f) of a cube, wherein each direction is associated with a separate Cartesian coordinate system with $X^{(a,b,c,d,e\ or\ f)}$, $Y^{(a,b,c,d,e\ or\ f)}$, $Z^{(a,b,c,d,e\ or\ f)}$ coordinates;
applying the following 6 true or false tests to each of the scan data points and associating each 3D scan data point to one of the 6 directions (a, b, c, d, e or f):

$$(X_{max}^{(a)} - |X_{mes}^{(a)}|) > Z_{mes}^{(a)} \wedge (Y_{max}^{(a)} - |Y_{mes}^{(a)}|) > Z_{mes}^{(a)}$$

$$(X_{max}^{(b)} - |X_{mes}^{(b)}|) > Z_{mes}^{(b)} \wedge (Y_{max}^{(b)} - |Y_{mes}^{(b)}|) > Z_{mes}^{(b)}$$

$$(X_{max}^{(c)} - |X_{mes}^{(c)}|) > Z_{mes}^{(c)} \wedge (Y_{max}^{(c)} - |Y_{mes}^{(c)}|) > Z_{mes}^{(c)}$$

$$(X_{max}^{(d)} - |X_{mes}^{(d)}|) > Z_{mes}^{(d)} \wedge (Y_{max}^{(d)} - |Y_{mes}^{(d)}|) > Z_{mes}^{(d)}$$

$$(X_{max}^{(e)} - |X_{mes}^{(e)}|) > Z_{mes}^{(e)} \wedge (Y_{max}^{(e)} - |Y_{mes}^{(e)}|) > Z_{mes}^{(e)}$$

$$(X_{max}^{(f)} - |X_{mes}^{(f)}|) > Z_{mes}^{(f)} \wedge (Y_{max}^{(f)} - |Y_{mes}^{(f)}|) > Z_{mes}^{(f)}$$

wherein max indicates a maximum leg length of the respective X, Y or Z axes, mes indicates a measured value of a scanned data point, and each of the data points is then assigned to the direction (a, b, c, d, e or f) for which the test outcome is true, the 6 directions a, b, c, d, e and f of the cube originate from a centrum, each viewing direction in the 3-dimensional heart model shown on the display unit passes through the centrum, and the centrum defines for each viewing direction a plane which crosses the centrum and which intersects the respective viewing direction perpendicularly, and
displaying the 3-dimensional heart model in a visualization on a display unit.

9. A method according to claim 8, wherein the action potential data are measured using an electrode assembly located at a distal portion of a mapping device, the action potential data are received from a mapping device in a control unit, displaying both the 3-dimensional heart model visualization and the processed data of the mapping device in a form of a model visualization of action potential data simultaneously on the display unit.

10. A method according to claim 8, further comprising, if for a given X, Y coordinate of a direction (a, b, c, d, e or f) more than one Z coordinate value exists, only the highest Z value is indexed for being displayed on the data output unit.

11. A method according to claim 8, wherein only those data points are visualized on the display unit that are located in a viewing direction located behind the plane.

12. A method according to claim 8, wherein each area of the 3-dimensional heart model visualization associated with a cube direction (a, b, c, d, e or f) is marked with an indicator which is one of a color and a pattern, the indicator being characteristic of the cube direction (a, b, c, d, e or f) associated with each such area.

13. A method according to claim 12, wherein the intensity of the indicator is increased in one of color intensity and pattern filling grade in the viewing direction.

14. A method according to claim 8, wherein a model visualization of an electrode assembly is displayed on the display unit together with the 3-dimensional heart model visualization.

* * * * *